Figure 1A:
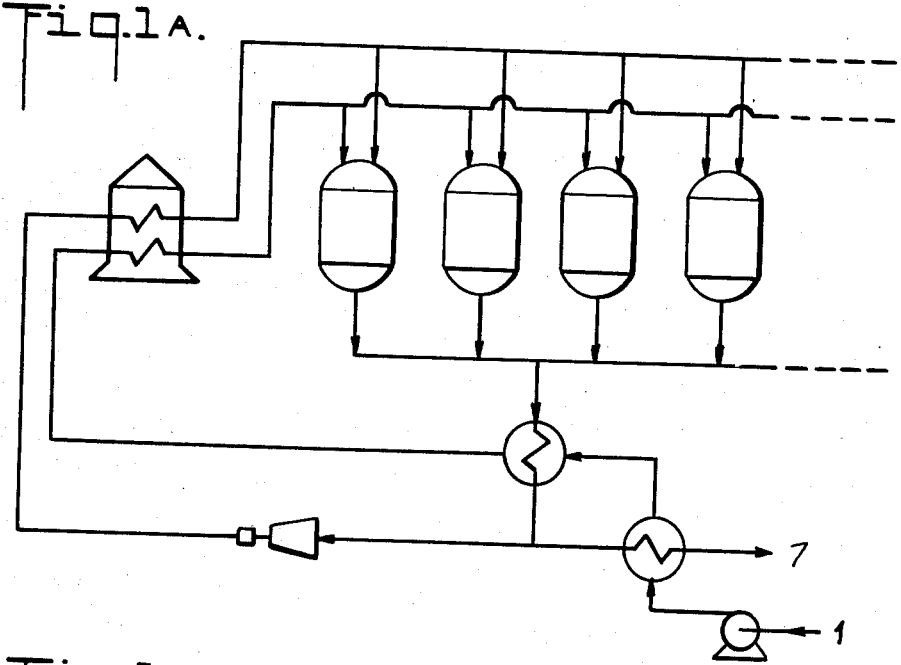

United States Patent [19]

Valladares Barrocas et al.

[11] 4,232,179
[45] Nov. 4, 1980

[54] PROCESS FOR PREPARING ETHENE

[75] Inventors: Helcio V Valladares Barrocas, Niteroi; Joao B. de Castro M. da Silva; Ruy Coutinho de Assis, both of Rio de Janeiro, all of Brazil

[73] Assignee: Petroleo Brasileiro S.A.-Petrobras, Rio de Janeiro, Brazil

[21] Appl. No.: 932,283

[22] Filed: Aug. 9, 1978

[30] Foreign Application Priority Data

Aug. 9, 1977 [BR] Brazil .............................. 7705256[U]

[51] Int. Cl.³ ................................................ C07C 1/24
[52] U.S. Cl. ..................................... 585/640; 585/639
[58] Field of Search ................. 260/682; 585/639, 640

[56] References Cited

U.S. PATENT DOCUMENTS

| | | | |
|---|---|---|---|
| 2,949,493 | 8/1960 | Happel et al. | 585/640 |
| 4,025,576 | 5/1977 | Chang et al. | 260/682 |
| 4,052,479 | 10/1977 | Chang et al. | |

FOREIGN PATENT DOCUMENTS

| | | | |
|---|---|---|---|
| 587378 | 4/1947 | United Kingdom | 260/682 |
| 186444 | 10/1966 | U.S.S.R. | 260/682 |

OTHER PUBLICATIONS

Winter et al., *Hydrocarbon Processing*, Nov., 1976, pp. 125-133.

*Primary Examiner*—C. Davis
*Attorney, Agent, or Firm*—Norbert P. Holler; Alfred H. Hemingway

[57] ABSTRACT

The object of the present invention is the preparation of ethene in the presence of catalysts using adiabatic reactors at high temperature. Such adiabatic reactors may be used in parallel or be disposed in series or arranged in parallel series assemblies or only a single reactor may be used.

The process of the invention allows the use of ethyl alcohol diluted with a sensible heat carrying fluid as feeding material. Said sensible heat carrying fluid is introduced into the reactor simultaneously with the feed, supplying the heat necessary for the performance of the reaction.

12 Claims, 3 Drawing Figures

PROCESS FOR PREPARING ETHENE

The present invention relates to the preparation of ethene, based on a process for dehydrating ethyl alcohol.

More particularly, the object of the invention is the production of ethene in the presence of catalysts, using adiabatic reactors and a high temperature. Such adiabatic reactors may be used in parallel or may be arranged in series or arranged in assemblies of parallel series, or still only a single reactor may be used.

The first records on dehydration of ethyl alcohol remounts to the XVIIIth Century, when ethene was obtained in the laboratory by passing ethyl alcohol over a heated catalyst. With the advent of plastic industry, ethene has become an essential raw material. In the thirties and forties of the present century several dehydrating units of ethyl alcohol were built which remained in operation up to the sixties.

However the situation was reversed due to appearing of processes for obtention of ethene from naphtha cracking. Ethene, instead of being obtained from ethyl alcohol is now the raw material for the manufacture of ethyl alcohol.

The world crisis of petroleum supply which occurred in 1973 brought as a consequence substantial increase in the cost of crude oil and its derivatives, thus rendering competitive the manufacture of ethene from ethyl alcohol. It may be thus foreseen that the methods which employ a renewable supply, such as alcohol obtained by fermentation of carbohydrates as raw material shall become more important in the future as the world petroleum reserves are being depleted.

The industrial processes for producing ethene by the dehydration of ethyl alcohol, are based on the passage of vapor of ethyl alcohol, over solid catalysts maintained at high temperature, employing multitubular, isothermal reactors.

Isothermic condition of these reactors, is achieved by the circulation of a heating fluid externally to the tubes. Such system, which employs indirect heating, besides showing some troubles in heat transfer, has some disadvantages both in its technical and economical aspects.

In the processes that utilize external circulation of heating fluid to maintain the reactor temperature, an additional limitation still occurs, relative to the thermal stability of the heating fluid. Presently known heating fluids are high boiling point and high thermal stability organic liquids or relatively low melting point inorganic salts. The more stable organic liquids may support maximum temperatures of about 370° C. On the other hand the fused salts may be heated up to about 550° C., presenting, however, serious shortcomings, such as for example, at temperatures lower than 150° C. they are solid materials, which implies in the possibility of serious operational problems in case that during the heating of the industrial units occur any failures, mainly, loss of circulation due to obstruction. Still other problems occur, such as, for example, those of equipment corrosion, mainly when a high purity grade salt is not used and, also, that of the material to be used in the equipment due to the fact that to work at temperatures above 450° C. only special steels may be used in the construction of the reactor. Another shortcoming in the utilization of fused salts as heating fluids, is the possibility of explosions, in the case of occurring the direct contact of fused salts with organic vapors.

The dehydration of ethyl alcohol is a highly endothermal reaction demanding an efficient heat exchange between the heating fluid and the reaction mixture so that it is possible to maintain the reactor temperature at proper levels and that the reaction may proceed with high conversion of the ethyl alcohol into ethene. The practical solution to provide the heat necessary for the reaction has been the use of a large number of small diameter tubes, in order to obtain greater heat exchange area. However, the use of a great amount of tubes which characterizes the so called multitubular reactor, presents certain technical and economical disadvantages. One disadvantage of that type of equipment is the necessity to work at low flow rate of ethyl alcohol in gaseous phase, when it is circulating inside the tubes, in order to obtain the heat necessary for the dehydrating reaction. There are still other problems, mainly concerning the sizing and engineering design of these multitubular reactors, being enough to mention, for example, that for an ethene production in order of 60,000 tons/year, there are required four isothermal reactors approximately 3 m in diameter and 9 m high, each containing about 1200 tubes.

Further as a consequence, the multitube reactors require high initial capital cost for large throughput industrial units.

On the other hand, it is already known through especialized technical literature that, in the catalytic dehydration of ethyl alcohol, ethene is produced by two distinct ways: the first one leading directly to the formation of the ethene, and the second one going through the intermediate ethyl ether formation, as shown in the scheme:

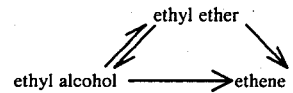

Thermodynamical study of the reactions above shows that the direct formation of the ethene is highly favoured at temperatures above 300° C. However, as part of the ethene is produced via ethyl ether, it is necessary to take into account the contact time of the reagents with the catalyst since for each temperature there exists an optimal operational condition. If the contact time is reduced, the yield is affected negatively, not only through reduction of the ethyl alcohol conversion yield into ethene, but also because of the appearing of ethyl ether among the reaction products. On the other hand, the kinetic study of the process shows that the higher the reaction temperature the lower will be the contact time with the catalyst in order that for a given conversion and selectivity, ethene be preferentially formed.

Beyond the limits established by the results of the thermodynamics and kinetics of the reactions still other limitative factors are to be considered in order to determine the optimum operating temperature. Among others, the following factors should be considered:

(a) the thermal decomposition of ethyl alcohol leading to the formation of coke and undesirable byproducts such as acetaldehyde, methane, ethane, etc.;

(b) formation of excess of byproducts on the catalyst surface, such as $C_3$ and $C_4$ hydrocarbons, and methane;

(c) deactivation of the catalyst through formation of coke on its surface and sintering.

An entirely new concept was now developed by us which solves fully the problems and shortcomings which occur in the processes already know.

One of the objects of this invention is to provide the supply of heat essential for the reaction, by introducing into the reactor, simultaneously with the feed, a sensible heat carrying fluid.

Another object of the present invention is the use of adiabatic reactors containing a fixed catalytic bed, said reactors could be arranged in series or arranged in form of parallel series assemblies, with or without intermediate injection of fresh feed between the reactors.

Another object of the present invention is to make possible the termination or start-up of the operation of one or more reactors, during normal processing of industrial units, without causing the interruption of ethene production.

Another object of the present invention is to provide the production of ethene via catalytic dehydration of ethyl alcohol, with high conversion of ethyl alcohol into ethene.

In the process of the present invention, the necessary heat to maintain the temperature of the catalyst bed at levels compatible with the desired conversion is supplied by the simultaneous introduction of the feed and the sensible heat carrying fluid. The heat carrying fluids mostly desired for the present process may be selected from: part of the effluent from the reactor used as recycle stream; steam supplied by an external source; other adequate fluids for the process, or any combination thereof.

In the pressent invention adiabatic ractors containing fixed catalyst bed are used; such adiabatic reactors may be used in parallel or may be disposed in series or arranged in form of assemblies of parallel series, or still only a single reactor may be used. This feature of the present invention allows that the operation of reactor, or series of reactors may be interrupted for the exchange or reposition of catalyst or maintenance services, without stopping the process continuity and not interfering with the performance of the other reactors.

In the most simple embodiment of the present invention, only one reactor is used and steam is employed as sensible heat carrying fluid.

The use of the effluent from the process as recycle stream eliminates the necessity of supplying steam to the process, bringing about economical advantages regarding the heat balance of the system, however implying, on counterpart, in the introduction of a compressor for the recycle. The arrangement including reactors in series with intermediate injection of fresh feed between the reactors, where the effluent stream from one reactor works as the sensible heat carrying fluid for the next reactor, as shown on FIGS. 1A and 1B, allows a dramatic reduction in consumption of steam in the process, and avoids utilizing of a recycle compressor, but requires a larger number of reactors. The choice among the various possibilities will depend of an economical balance, taking into consideration the desired yield of ethene, as well as the existing facilities for steam generation on the area where the industrial unit is to be installed.

Having in mind the entirely new features of the present invention which render it substantially different from the conventional processes, as for example, the simultaneous introduction of the feed and of a sensible heat carrying stream the following advantages are noted:

(a) the reactors in the process of the invention are adiabatic containing catalyst fixed beds, comprising, therefore, simpler vessels regarding its mechanical construction, since, due to particular concept of the process, there is no more necessity to use multitubular reactors, which represents substantial saving in the initial capital cost if compared to the high cost of the reactors used in processes known before;

(b) as in the process of the present invention there is no need of heating fluid circulation, there is no restriction on the efficiency of thermal exchange, heating fluid stability and operational safety problems, existing in the processes of the previous art;

(c) as immediate consequence of the above advantages, resulting from the entirely new concept of the process of the present invention, higher temperatures may be used in the reactor and, therefore, higher space velocities may be used, which brings about an additional decrease in process costs due to the smaller size of the reactors and the lower consumption of catalyst.

Other advantages of the process, keeping in mind the particularities of the invention previously cited, is to provide means to compensate the gradual loss of catalyst activity, unavoidable in catalytic processes. Besides presenting lower loss of catalyst activity, the process of the present invention, when compared with conventional catalytic processes, presents the advantage of allowing compensation for the gradual loss of catalyst activity due to the following characteristics or any combination thereof:

(a) increase of the preheating temperature of the feed or of the sensible heat carrying stream, in order to increase the temperature at the top of the reactor;

(b) increase of the ratio between the sensible heat carrying stream and the feed thus rising the reactor bottom temperature;

(c) reduction of the space velocity related to the fresh feed, in order to increase the time of contact between the feed and the catalyst.

Another advantage of the invention is to allow the use of diluted ethyl alcohol in the sensible heat carrying fluid stream. This feature of the invention leads to considerable reduction both in the formation of $C_3$ and $C_4$ byproducts as well as in the deposition of coke over the catalyst, these peculiar features leading to the obtention of highly pure ethene.

As a result, the process of the present invention allows longer operating periods without need of changing the catalyst than in the case of known processes which use as a feed undiluted ethyl alcohol. The limitations concerning the maximum operating temperature even considering the problem caused by the catalyst stability and still having in mind the obtention of high grade product, are yet much smaller for the process of the invention still allowing the use of rather high temperature values than that used in the conventional processes.

The catalysts that can be used in the process of the present invention, comprise those of the previous art already known such as alumina, silica-alumina, silica, refractory metal oxides such as for example those of titanium, hafnium, zirconium, tungsten etc.; zeolites, phosphoric acids supported on carbon, calcium phosphates and molybdates etc. However the prefered catalysts for the process of this invention are alumina and silica alumina.

Figure 1B:
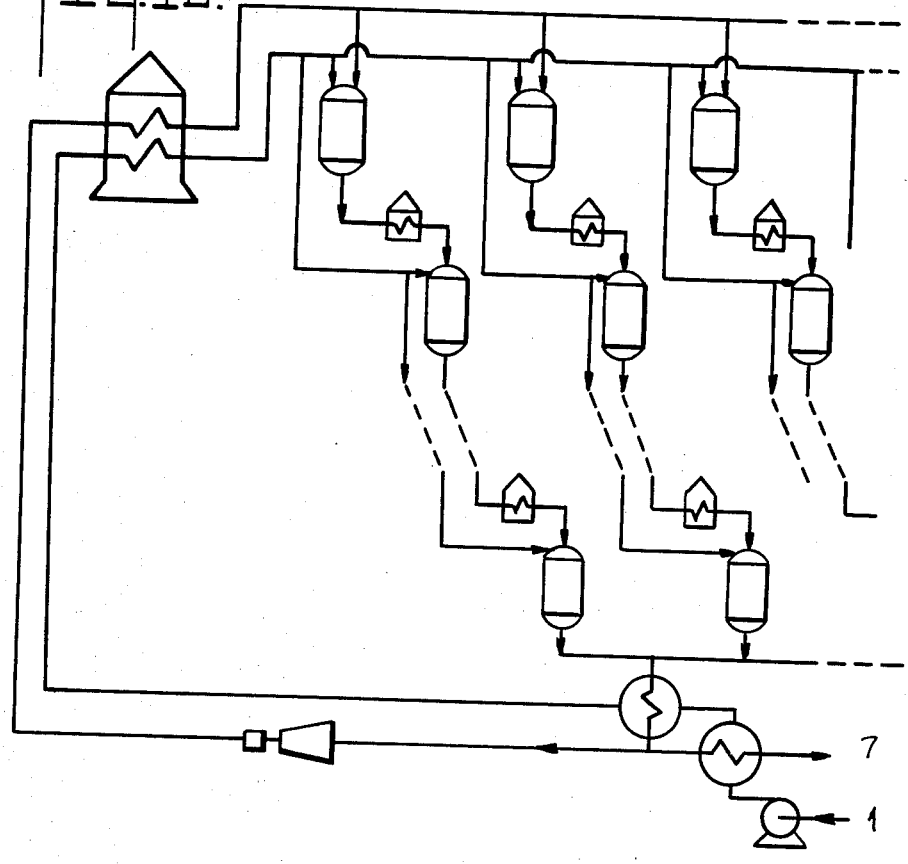
Figure 2:
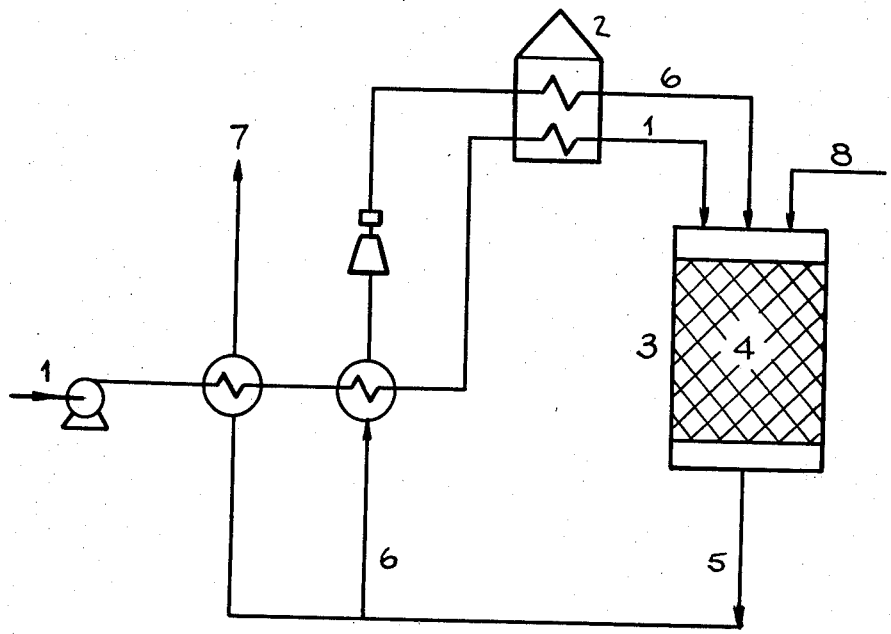

For better understanding of the invention, the process shall be hereinafter described in accordance to the flow sheets presented in FIGS. 1A, 1B and 2.

Ethyl alcohol (1) is heated by indirect heat exchange for example in a furnace (2) up to a temperature in the range from 180° to 600° C., preferably in the range between 300° and 500° C., being then sent to an adiabatic reactor (3), which internally contains a catalyst fixed bed (4), said adiabatic reactor operating in the pressure range between 0.2 and 20 kg/cm² absolute, while said catalyst bed (4) is maintained in the temperature range between about 600° C. (maximum temperature on top of the bed) and about 180° C. (minimum temperature in the bottom of the bed) by means of sensible heat carrying stream. Said sensible heat carrying stream is heated in the furnace (2) to a temperature up to 800° C. As it was previously defined said sensible heat carrying stream may be comprised by the recycle (6) of part of the effluent (5) of said reactor (3), the effluent from one of previous reactors (FIGS. 1A and 1B), steam, heated inert gas or any combination thereof (8).

The stream (5) which flows out from the adiabatic reactor (3) is split, in case of using recycle for carrying sensible heat, into two streams: the recycle stream (6) which, after exchanging heat with the feed, passing through a compressor and being heated in the furnace (2), shall be reintroduced into the reactor; the other stream after exchanging heat with the feed will be sent to the ethene purification step (7) or will be used as a sensible heat carrier for one of the next reactors of the series.

In the process of the invention the ratio between the sensible heat carrying stream and the feed may range from 0.2:1 to 20:1, but preferably shall be comprised within the range from 0.2:1 to 10:1. On the other hand the space velocity may range between 10 and 0.01 g/h of ethyl alcohol per gram of catalyst, depending on the desired operation severity, the range between 1.0 and 0.01 g/h/g being particularly preferred.

Some of the examples will be disclosed hereinafter with the exclusive purpose of showing the operation and efficiency of the process, without limiting the invention.

Tables I, II, refer to examples 1 to 8 and they disclose the operating conditions and results in terms of ethyl alcohol conversion and of the reactor effluent gas composition from several runs in which a commercial silica-alumina catalyst has been employed. In all those runs the sensible heat carrying stream was the recycle of part of the adiabatic reactor effluent.

TABLE I

| | Operating Condition in runs using silica-alumina catalyst | | | |
|---|---|---|---|---|
| Example | Pressure (kg/cm² gauge) | Bed temperature (°C.)* | Space velocity ** | Recycle ratio *** |
| 1 | 0.84 | 400–300 | 0.07 | 2.82 |
| 2 | 0.84 | 400–320 | 0.05 | 3.60 |
| 3 | 0.84 | 400–320 | 0.03 | 7.15 |
| 4 | 0.84 | 420–320 | 0.11 | 3.00 |
| 5 | 3.50 | 400–300 | 0.11 | 3.00 |
| 6 | 3.50 | 440–340 | 0.11 | 3.00 |
| 7 | 7.00 | 440–300 | 0.11 | 3.00 |

*The temperatures indicated correspond respectively to catalyst bed inlet and outlet temperatures.
**Space velocity relating to alcohol stated in g/h of ethyl alcohol per g of catalyst.
***Recycle ratio, stated in weight of ethene plus steam per weight of alcohol in the feed to adiabatic reactor.

TABLE II

| | Results of runs listed in Table I | | | | | | | |
|---|---|---|---|---|---|---|---|---|
| Examples | 1 | 2 | 3 | 4 | 5 | 6 | 7 | 8 |
| Conversion (%)* | 97.70 | 98.60 | 95.25 | 92.50 | 93.91 | 96.50 | 95.66 | 96.33 |
| Composition of the effluent (%/W)** Methane | 0.05 | 0.08 | 0.11 | 0.05 | 0.02 | 0.10 | 0.07 | 0.07 |
| Ethene | 89.19 | 87.78 | 78.52 | 80.48 | 96.63 | 95.20 | 96.16 | 97.29 |
| Ethane | 4.48 | 6.55 | 7.91 | 2.76 | 1.22 | 2.24 | 2.13 | 1.33 |
| C₃ | 0.17 | 0.19 | 0.24 | 0.12 | 0.10 | 0.28 | 0.25 | 0.19 |
| Acetaldehyde | 1.21 | 1.82 | 1.12 | 0.79 | 0.30 | 0.62 | 0.15 | 0.16 |
| C₄ | 0.34 | 0.56 | 0.44 | 0.25 | 0.50 | 0.70 | 0.73 | 0.51 |
| Ethanol | 4.03 | 2.36 | 7.73 | 12.33 | 0.68 | 0.06 | — | — |
| Ethyl Ether | 0.52 | 0.67 | 3.92 | 3.24 | 0.55 | 0.80 | 0.51 | 0.45 |

*Conversion expressed in (alcohol in the feed minus non reacted alcohol/alcohol in the feed.)
**Examples 1 to 4: composition of total effluent
Examples 5 to 8: composition of gaseous effluent Tables III and IV refer to Examples 4 to 13 and they show the operating conditions and results in terms of ethyl alcohol conversion and composition of the reactor gas effluent in which an alumina catalyst was employed. In these runs, steam was employed as the sensible heat carrying stream and no recycle was used.

TABLE III

| Example | Pressure (kg/cm² gauge) | Temperature (°C.) | Space Velocity (g/h/g) | Steam/feed ratio |
|---|---|---|---|---|
| 9 | 1.75 | 390–355 | 0.70 | 4.50 |
| 10 | 3.00 | 390–355 | 0.70 | 4.50 |
| 11 | 3.00 | 370–330 | 0.34 | 5.00 |
| 12 | 7.00 | 390–355 | 0.30 | 4.25 |
| 13 | 7.70 | 470–360 | 0.30 | 3.00 |

TABLE IV

| Results of the runs performed under conditions specified in Table III | | | | | |
|---|---|---|---|---|---|
| Example | 9 | 10 | 11 | 12 | 13 |
| Conversion | 98.0 | 90.0 | 94.0 | 97.5 | 99.9 |
| Composition of gaseous effluent Methane | 0.01 | 0.02 | 0.01 | 0.02 | 0.02 |
| Ethene | 99.21 | 98.73 | 99.01 | 98.93 | 99.44 |
| Ethane | 0.70 | 1.07 | 0.88 | 0.78 | 0.16 |

TABLE IV-continued

Results of the runs performed under conditions specified in Table III

| Example | | 9 | 10 | 11 | 12 | 13 |
|---|---|---|---|---|---|---|
| (% weight) | $C_3$ | 0.08 | 0.18 | 0.10 | 0.27 | 0.20 |
| | Acetaldehyde | — | — | — | — | 0.05 |
| | $C_4$ | — | — | — | — | 0.14 |
| | Ethanol | — | — | — | — | — |
| | Ethyl Ether | — | — | — | — | — |

Table V shows the results of Examples 14 and 15, carried out under pressure of 0.84 kg/cm² (gauge), reactor temperature (inlet and outlet) in the range of 460°–360° C., space velocity related to ethyl alcohol is 0.25 g/h/g, following the ratio diluent/feed equal to 2.75. In these runs alumina catalyst was used but, as a sensible heat carrying stream (diluent) a combination of inert gas and steam was used in Example 14 and recycle from the effluent was employed in Example 15.

TABLE V

Runs performed with different types of diluents

| Example | | 14 | 15 |
|---|---|---|---|
| Diluent | | $N_2 + H_2O$ | Recycle |
| | Conversion | 99.8 | 99.9 |
| Effluent | Methane | 0.01 | 0.02 |
| composition | Ethene | 97.46 | 98.95 |
| (% by weight) | Ethane | 0.09 | 0.63 |
| | $C_3$ | 0.17 | 0.09 |
| | Acetaldehyde | 0.83 | 0.19 |
| | $C_4$ | 1.05 | 0.12 |
| | Ethanol | 0.38 | — |
| | Ethyl Ether | — | — |

Tables VI and VII, show the operating conditions and results of the Example 16, in which two adiabatic reactors were used, such reactors being arranged in series with the introduction of fresh feed between them.

As sensible heat carrying fluid, steam was used in the first reactor and the total effluent of the first reactor was employed in the second reactor.

TABLE VI

| Operating conditions of reactors connected in series | |
|---|---|
| Outlet pressure from 2nd reactor | 7.0 kg/cm², gauge |
| Temperature of 1st. reactor (inlet and outlet) | 470°–360° C. |
| Temperatures of 2nd reactor (inlet and outlet) | 470°–360° C. |
| Ratio steam/feed in 1st. reactor | 3.00 |
| Ratio effluent from 1st. reactor/feed to 2nd reactor | 2.67 |
| Space velocity of the feed in 1st. reactor | 0.30 g/h/g |
| Space velocity of the fresh feed in 2nd reactor | 0.30 g/h/h |

TABLE VII

| Composition of the effluent gas from 2nd reactor (% by weight) | |
|---|---|
| Methane | 0.19 |
| Ethene | 97.30 |
| Ethane | 0.23 |
| $C_3$ | 1.40 |
| Acetaldehyde | 0.11 |
| $C_4$ | 0.68 |
| Ethanol | — |
| Ethyl Ether | 0.09 |

We claim:

1. Process for preparing ethene by dehydrating ethyl alcohol in the presence of catalyst, characterized in that ethyl alcohol is heated by indirect heat exchange, up to a temperature in the range from 180°–600° C., introducing thus heated ethyl alcohol into one or more adiabatic reactors containing in its interior a catalyst fixed bed, said adiabatic reactor being maintained in a pressure range between 0.2 and 20 kg/cm² absolute, and said fixed catalyst bed being maintained at a temperature comprised within the range from 600° C. on the top to 180° C. in the bottom, by means of a sensible heat carrying stream heated up to a temperature up to 800° C., the weight ratio between the sensible heat carrying fluid stream and the stream of ethyl alcohol varies within a 0.2:1 to 20:1 range, and the ratio between the amounts of ethyl alcohol and the catalyst is comprised within a range from 10 to 0.01 g/h of ethyl alcohol per gram of catalyst; removing the effluent from said adiabatic reactor and sending the same to the purification step.

2. Process for preparing ethene in accordance to claim 1, characterized in that the heat required for the dehydrating reactions is supplied to the process by means of a sensible heat carrying fluid introduced in the adiabatic reactor simultaneously with the feed.

3. Process for preparing ethene in accordance to claim 2, characterized in that the sensible heat carryng fluid is selected from at least one of the following: part of the adiabatic effluent used as recycle stream, steam provided by an external source, and heated inert gas provided by an external source.

4. Process for preparing ethene in accordance to claim 1, characterized in that ethyl alcohol is heated by indirect heat exchange up to a temperature in the range from 180° to 600° C., thus introducing the heated ethyl alcohol into one or more adiabatic reactors containing in its interior a fixed catalyst bed, said adiabatic reactor being maintained within a pressure range between 0.2 an 20 kg/cm² absolute, and said fixed catalyst bed being maintained within a temperature range from 600° C. on top to 180° C. in the bottom by means of sensible heat carrying fluid previously heated to a temperature up to 800° C. said heated fluid being selected from an inert gas, steam or a combination of inert gas and steam, the weight ratio between the sensible heat carrying fluid stream and the ethyl alcohol stream varies within the range from 0.2:1 to 20:1 and the ratio between the amounts of ethyl alcohol and the catalyst is comprised within a range from 10 to 0.01 g/h of ethyl alcohol per gram of catalyst; removing the effluent from said adiabatic reactor and sending it to purification stage.

5. Process for preparing ethene, in accordance to claim 1, characterized in that the ethyl alcohol is heated through indirect heat exchange within the temperature range from 180° to 600° C., introducing the thus heated ethyl alcohol into one or more adiabatic reactors containing internally a catalyst fixed bed, said adiabatic reactor being maintained within absolute pressure range between 0.2 and 20 kg/cm² and said catalyst fixed bed being maintained at a temperature comprised within the range from 600° C. on the top to 180° C. in the bottom through a recycle stream as a sensible heat carrying fluid, separating the effluent from said adiabatic reactor into two streams one of them after exchanging heat with ethyl alcohol being introduced into the adiabatic reactor and going through a compressor being reheated to a temperature up to 800° C. and introduced into the adiabatic reactor as said recycled stream and the other portion of the effluent being sent after having exchanged heat with ethyl alcohol which will be introduced into the adiabatic reactor, to the ethene purification stage, the weight ratio between the sensible heat carrying fluid and the ethyl alcohol stream varying within the range from 0.2:1 to 20:1 and the ratio between the amounts of ethyl alcohol and catalyst being comprised within a range between 10 g and 0.01 g/h of ethyl alcohol per gram of catalyst.

6. Process for preparing ethene, in accordance to claims 1 or 4 or 5, characterized in that the catalyst which comprises the fixed bed inside said adiabatic reactors is selected from silica, alumina, silica-alumina, refractory metal oxides, zeolites, phosphoric acid supported on carbon, calcium phosphates and calcium molybdates.

7. Process for preparing ethene, in accordance to claims 1 or 4 or 5, characterized in that the catalyst comprising said fixed bed inside said adiabatic reactors is selected from the group consisting of silica-alumina and alumina.

8. Process for preparing ethene, in accordance to claims 1 or 4 or 5, characterized in that the reaction is carried out in a single adiabatic reactor.

9. Process for preparing ethene, in accordance to claims 1 or 4 or 5 characterized in that the reaction is carried out in adiabatic reactors arranged in parallel.

10. Process for preparing ethene, in accordance to claims 1 or 4 or 5, characterized in that the reaction is carried out in adiabatic reactors forming assemblies of parallel series.

11. Process for preparing ethene, in accordance to claims 1, 4 or 5, wherein said ethyl alcohol is heated by said indirect heat exchange to a temperature within the range 300°–500° C.

12. In a process for preparing ethene by the dehydration of ethanol, the improvement which comprises providing the required heat for the reaction directly to the reaction by means of simultaneously introducing the ethanol feed and a heat-carrying fluid into at least one adiabatic reactor containing a fixed bed catalyst.

* * * * *

REEXAMINATION CERTIFICATE (789th)

United States Patent [19]
Valladares Barrocas et al.

[11] B1 4,232,179
[45] Certificate Issued   Dec. 8, 1987

[54] PROCESS FOR PREPARING ETHENE

[75] Inventors: Helcio V. Valladares Barrocas, Niteroi; Joao B. de Castro M. da Silva; Ruy Coutinho de Assis, both of Rio de Janeiro, all of Brazil

[73] Assignee: Petroleo Brasileiro S.A.-Petrobras, Rio de Janeiro, Brazil

Reexamination Request:
   No. 90/000,378, May 9, 1983

Reexamination Certificate for:
   Patent No.:   4,232,179
   Issued:       Nov. 4, 1980
   Appl. No.:    932,283
   Filed:        Aug. 9, 1978

[30] Foreign Application Priority Data

Aug. 9, 1977 [BR]   Brazil ............................. 7705256[U]

[51] Int. Cl.$^4$ ................................................. C07C 1/24
[52] U.S. Cl. ...................................... 585/640; 585/639

[56] References Cited

U.S. PATENT DOCUMENTS 1,909,356  5/1933  Jaeger .

FOREIGN PATENT DOCUMENTS 516360  1/1940  United Kingdom .

OTHER PUBLICATIONS

S. A. Puranik and M. M. Sharma, "Vapour Phase Dehydration of Ethanol", Jul. 1967, Indian Chemical Engineer, pp. 124–135.

Primary Examiner—C. Davis

[57]         ABSTRACT

The object of the present invention is the preparation of ethene in the presence of catalysts using adiabatic reactors at high temperature. Such adiabatic reactors may be used in parallel or be disposed in series or arranged in parallel series assemblies or only a single reactor may be used.

The process of the invention allows the use of ethyl alcohol diluted with a sensible heat carrying fluid as feeding material. Said sensible heat carrying fluid is introduced into the reactor simultaneously with the feed, supplying the heat necessary for the performance of the reaction.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–12 are cancelled.

* * * * *